(12) United States Patent
Fan et al.

(10) Patent No.: US 7,259,131 B2
(45) Date of Patent: Aug. 21, 2007

(54) MILD, MOISTURIZING CLEANSING COMPOSITIONS

(75) Inventors: Shimei Fan, Inverness, IL (US); Esther Kim, Woodridge, IL (US); Todd M. Kruse, Oak Park, IL (US); Tirucherai V Vasudevan, Lake Zurich, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 97 days.

(21) Appl. No.: 10/894,891

(22) Filed: Jul. 20, 2004

(65) Prior Publication Data
US 2006/0019846 A1 Jan. 26, 2006

(51) Int. Cl.
*A61K 7/00* (2006.01)
*A61K 7/06* (2006.01)

(52) U.S. Cl. .................. 510/119; 510/122; 510/123; 510/124; 510/125; 510/127; 510/130; 510/426; 510/490; 424/70.13

(58) Field of Classification Search ............... 510/119, 510/123, 125, 130; 424/70.11, 70.1, 70.12, 424/70.21
See application file for complete search history.

(56) References Cited

U.S. PATENT DOCUMENTS

| | | | |
|---|---|---|---|
| 3,328,314 A | 6/1967 | Marquis | |
| 4,426,310 A | 1/1984 | Verunica | |
| 4,668,422 A | 5/1987 | Malik et al. | |
| 4,839,098 A | 6/1989 | Wisotzki et al. | |
| 5,376,310 A * | 12/1994 | Cripe et al. | 510/235 |
| 5,811,087 A | 9/1998 | Mohring et al. | |
| 6,087,320 A | 7/2000 | Urfer et al. | |
| 6,165,454 A | 12/2000 | Patel et al. | |
| 6,169,060 B1 | 1/2001 | Taniuchi | |
| 6,207,142 B1 | 3/2001 | Odds et al. | |
| 6,284,230 B1 * | 9/2001 | Sako et al. | 424/70.11 |
| 6,306,805 B1 | 10/2001 | Bratescu et al. | |
| 6,514,490 B2 | 2/2003 | Odds et al. | |
| 6,903,064 B1 * | 6/2005 | Kasturi et al. | 510/433 |
| 2003/0003070 A1 | 1/2003 | Eggers et al. | |
| 2004/0234484 A1 * | 11/2004 | Peffly et al. | 424/70.13 |

FOREIGN PATENT DOCUMENTS

| | | |
|---|---|---|
| GB | 2 255 101 | 10/1992 |
| WO | 93/25650 | 12/1993 |
| WO | 01/06997 | 2/2001 |
| WO | WO 01/06997 * | 2/2001 |

OTHER PUBLICATIONS

Applicant: Kruse et al. Case No. J6914(C) Serial No. To be assigned Title: Mild, Moisturizing Sulfosuccinate Cleansing Compositions.
Applicant: Fan et al. Case No. J6910(C) Serial No. To be assigned Title: Mild, Moisturizing Cleansing Compositions With Improved Storage Stability.
Int'l. Search Report No. PCT/EP 2005/007019 dated Nov. 29, 2005—3 pp.
Written Opinion for Int'l. Application No. PCT/EP 2005/007019 dated Nov. 29, 2005—7 pp.

* cited by examiner

*Primary Examiner*—Necholus Ogden
(74) *Attorney, Agent, or Firm*—Michael P. Aronson

(57) ABSTRACT

Compositions used for cleansing hair and skin based on the combination of a sulfosuccinate surfactant and an amphoteric surfactant are described that are very mild but do not compromise in-use properties and economy. A route to solve the intrinsic instability of such aqueous compositions in storage has been developed based on the use of sulfosuccinic acid or a salt of sulfosuccinic acid present in an amount of at least about 4% based on the weight of the sulfosuccinate surfactant.

1 Claim, No Drawings

MILD, MOISTURIZING CLEANSING COMPOSITIONS

FIELD OF INVENTION

The present invention is directed at mild cleansing compositions that have desirable in-use properties such as lather, provide excellent moisturizing and conditioning benefits to hair and skin and are stable in storage.

BACKGROUND OF INVENTION

Cleansing compositions that are mild to the hair and skin and are perceived to provide the sensory attributes that consumers associate with healthy, moisturized hair and skin have become increasingly popular in recent years.

Although various mild surfactant systems have been proposed as the basis of such cleansing compositions there is generally a trade-off between the mildness of a composition and its ability to produce a rich abundant lather. Consequently when using mild surfactants, formulators often increase the total surfactant content to overcome this lather deficiency. Not only does this adversely affect the economics of the composition but this can also reduce the mildness of the composition since the ability of a surfactant to interact with the proteins present in hair and skin depends on the total surfactant concentration in addition to other factors. Furthermore, high concentrations of surfactants can also interfere with the efficient delivery of insoluble hair and skin conditioning agents that are desirable to incorporate in moisturizing shampoo compositions.

Thus there remains a need for surfactant compositions that are mild to hair and skin and yet are efficient in terms of producing a rich, abundant lather without the need to use excessive levels of surfactant in the composition and which are highly compatible with insoluble hair conditioning agents.

While studying a variety of mild cleansing compositions, it has been found that binary mixtures of certain sulfosuccinate surfactants and amphoteric surfactants used alone or in further combination with alkyl ethoxy sulfates and other surfactants can provide highly efficient and mild shampoo and skin cleansing bases. However, these bases had highly variable and unpredictable storage stability. Some combinations became very viscous, even gelling during storage and were unacceptable to consumers while others having what appeared to be the same "nominal" composition did not.

Extensive study and chemical analysis indicated that it was the interaction of hydrolysis products of the sulfosuccinate surfactant with the amphoteric surfactant that was responsible for the anomalous thickening in storage. Furthermore it was surprisingly found that the level of sulfosuccinic acid or its simple salt that was present in the composition had a pronounced and critical effect on storage stability, especially under high temperature storage conditions. These findings provided the basis for making practical shampoo and skin cleansing compositions that employ a sulfosuccinate surfactant in combination with an amphoteric surfactant. These combinations have the advantage of providing very mild compositions that do not compromise lather, are efficient and economical and are highly compatible with hair and skin conditioning agents.

These and other advantages of the compositions disclosed herein will become clear from the description of the invention.

The following patents and publications have been considered:

WO93/25650 discloses highly concentrated (30-90%) surfactant concentrates that include an alkyl polyglycoside and an effective amount of a viscosity-adjusting agent selected from the group consisting of inorganic and organic electrolytes. Carboxylic acids and their salts are mentioned as organic electrolytes.

U.S. Pat. No. 4,668,422 describes compositions based on alkylpolyglycosides and amphoteric surfactants with optional small amounts of anionic surfactant. Sodium chloride and ammonium chloride are disclosed as viscosifying agents, i.e., materials that increase the viscosity of the composition.

U.S. Pat. No. 4,839,098 discloses a liquid dishwashing detergent consisting essentially of alkyl glucoside and dialkylsulfosuccinate. Ammonium chloride is disclosed as a viscosity regulator.

U.S. Pat. No. 6,165,454 discloses a low energy method for making hair care products including an anionic surfactant, a water insoluble silicone and an acrylic stabilizing agent.

U.S. Pat. No. 6,306,805 discloses surfactant compositions that include a cationic surfactant, an anionic surfactant and a bridging surfactant.

The present invention seeks improvements over deficiencies in the known art. Among the one or more problems addressed include storage instability.

SUMMARY OF THE INVENTION

The subject invention provides a composition that is mild to hair and skin, has excellent lather and is highly efficient in terms of the relatively low total surfactant content required.

More specifically, the mild aqueous composition which is highly suitable for cleansing hair and skin includes:

i) from about 1% to about 20% of a sulfosuccinate surfactant, ii) from about 1% to about 20% of an amphoteric surfactant, and iii) a sulfosuccinic acid or a salt of a sulfosuccinic acid, wherein the sulfosuccinic acid or the salt of sulfosuccinic acid is present in an amount of at least about 4% based on the weight of the sulfosuccinate surfactant.

In a second preferred embodiment of the invention, the binary sulfosuccinate/amphoteric surfactant mixture is further combined with an additional anionic surfactant or surfactants, which preferably contains at least one surfactant that is an alkyl ethoxy sulfate.

DETAILED DESCRIPTION OF THE INVENTION

As used herein % or wt. % refers to percent by weight of an ingredient as compared to the total weight of the composition or component, that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps or options need not be exhaustive.

The present invention relates to mild compositions suitable for cleansing human hair and skin. The composition includes a surfactant system, sulfosuccinic acid or its salt and various optional hair and/or skin care additives, and adjuncts. These components are discussed in detail below.

Surfactant System

The surfactant system is composed of the combination of two essential types of surfactants: one is a sulfosuccinate anionic surfactant and the other is an amphoteric surfactant.

The sulfosuccinate anionic surfactant is preferably the half ester having the general formula:

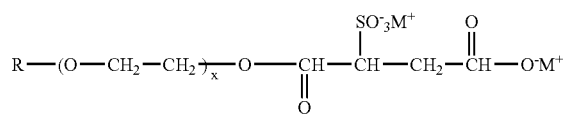

where R is a straight or branched chain alkyl or alkenyl group having 10 to 22 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Preferred sulfosuccinate surfactants include $C_{10}$-$C_{14}$ sulfosuccinate, and $C_{10}$-$C_{14}$ ethoxy (1-5) sulfosuccinate. Laureth-3 sulfosuccinate is an especially preferred sulfosuccinate surfactant.

The level of sulfosuccinate surfactant present in the composition can be in the range from about 1% to about 20% by weight of the composition, preferably about 1% to about 10%, and most preferably from about 1.5% to about 7% of the composition.

The second essential component of the surfactant system is an amphoteric surfactant.

An especially preferred amphoteric surfactant is a betaine surfactant having the following general chemical formula:

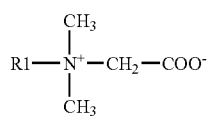

where R1 is either an alkyl or an alkyl amidoalkyl group. The alkyl group in either case can be a branched or a straight chain alkyl group having 8-18 carbon atoms, preferably 10-16 carbon atoms and most preferably 10-14 carbon atoms. Available betaines include oleyl betaine, caprylamidopropyl betaine, lauramidopropyl betaine, isostearylamidopropyl betaine, and coco imidoazolinium betaine.

Particularly preferred betaines are lauryl or coco betaine, and lauryl or coco amidopropyl betaine. The term "lauryl" refers to predominantly a fatty acid of $C_{12}$ chainlength while coco refers to a mixture of $C_{12}$ and $C_{14}$ chainlength fatty acids.

A second type of suitable amphoteric surfactant is an hydroxysultaine (CTFA name for a sulfobetaine having the hydroxypropyl sulfonate group) which are generally formed from the reaction of a tertiary amine with epichlorohydrin and a bisulfite. Their general formula is:

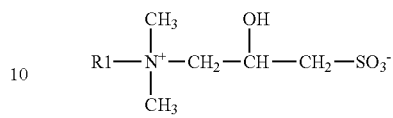

where R1 is either an alkyl or an alkyl amidoalkyl group. The alkyl group in either case can be a branched or a straight chain alkyl group having 8-18 carbon atoms, preferably 10-16 carbon atoms and most preferably 10-14 carbon atoms. Commercially available sultaines include: lauryl hydroxy sultaine, tallowamidopropyl hydroxy sultaine, erucamidopropyl hydroxy sultaine, and alkylether hydroxypropyl sultaine.

Preferred hydroxysultaines are coco and laurylamidopropyl hydroxy sultaine and coco amidopropyl hydroxysultaine.

Another class of amphoteric surfactants is formed by the reaction of imidazoline with chloroacetic acid. This class includes the fatty amphoacetates and fatty amphodiacetates having the general formula shown below. These materials were formally known as amphoglycinates and amphocarboxyglycinates respectively.

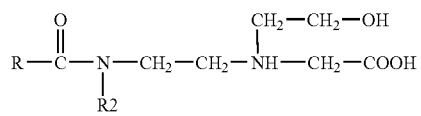

where R is a straight or a branched chain alkyl chain having 10 to 16 carbon atoms and R2 is either H or a —CH2—COOH.

Preferred amphoacetates are coco and lauro amphoacetate and preferred amphodiacetates are lauro and coco amphodiacetate.

Other less preferred amphoteric surfactants include $C_{10}$-$C_{16}$ fatty amphocarboxy propionates and $C_{10}$-$C_{16}$ fatty amphopropionates.

Another class of amphoteric surfactant is fatty amine oxide such as lauryl dimethyl amine oxide. These surfactants have been classified by various workers as "nonionic" surfactants, "cationic" surfactants, and "amphoteric" surfactants. The N-oxide group is a weak base having a $pk_b$ of about 9. Thus, at pH of 5 about 50% of the molecules exist as the positive $N^+$—OH species, while at pH 6.5 only about 3% exists as the positively charged species. For the purposes of the present invention, fatty amine oxides are classified as amphoteric surfactants The level of amphoteric surfactant present in the composition can be in the range from about 1% to about 20% by weight of the composition, preferably about 1% to about 10%, and most preferably from about 1.5% to about 5.5% of the composition.

The ratio of sulfosuccinate surfactant to amphoteric surfactant is preferably in the range from about 2:1 to about 1:2, more preferably from about 1.5:1 to about 1:1.25, and most preferably from about 1.5:1 to about 1:1.

A variety of optional surfactants which are suitable for cleansing human hair and skin can also be included in the composition provided they do not excessively compromise the mildness of the composition. These include anionic surfactants such as acyl isethionates, alkyl sulfates, alkyl ethoxy sulfates, fatty sarcosinates, alkyl taurates and various amino acid based amido carboxylates; non-ionic surfactants such as alcohol ethoxylates, fatty amides, alkyl (poly)saccharides, and alkyl glucamides; and cationic surfactants such as long chain fatty amines and long chain fatty ethoxylated amines.

A particularly preferred optional surfactant is an alkyl ethoxy sulfate having the general formula

$$R3\text{-}(O\text{---}CH_2\text{---}CH_2\text{---})_x\text{---}O\,SO_3\,M$$

wherein R3 is an alkyl group having a straight or branched alkyl chain. The alkyl group can contain 8-20 carbon atoms, preferably 10-18 carbon atoms and most preferably 12-15 carbon atoms. "X" represents the average ethylene oxide content per surfactant molecule and can in principle be in the range from about 0.5 to about 10, preferably from about 0.5 to about 5 and most preferably between about 0.5 and about 3.5.

In one embodiment of the invention the alkyl ethoxy sulfate surfactant can be a $C_{10}$-$C_{22}$ alkyl ethoxy sulfate surfactant having 1 to about 5 ethylene oxide groups.

"M" represents a cation, preferably a monovalent cation, and most preferably sodium, ammonium or alkanolammonium ion.

The alkyl ethoxy sulfate can be present is the composition in an amount ranging from about 1% to about 25%, preferably about 4% to about 12%, and most preferably about 4% to about 8% based on the total weight of the composition.

In one embodiment of the invention the weight ratio of the alkyl ethoxy sulfate surfactant to the sulfosuccinate surfactant is in the range from about 2:1 to about 1:1.

The total surfactant content of the compositions of the instant invention can range from about 1 to about 30% by weight. However, since the compositions are directed at end-use hair and skin cleansing by consumers and not as concentrates, the surfactant content is preferably about 3 to about 25% and most preferably about 4% to about 15%.

Sulfosuccinic Acid or Sulfosuccinate Salt

It has been surprisingly found that sulfosuccinic acid or the sodium, potassium, ammonium, or alkanolamonnium salt of sulfosuccinic acid greatly improves the long term stability of compositions that combine an sulfosuccinate surfactant with an amphoteric surfactant. Weight of sulfosuccinic acid is conveniently expressed as the ratio of sulfosuccinic acid (or the stoichiometric equivalent of sulfosuccinic acid in the case of its salt) to that of the total weight of the sulfosuccinate surfactant times 100. This number is designated herein as the "% (or "percent") sulfosuccinic acid relative to the total weight of the sulfosuccinate surfactant present. The % sulfosuccinic acid should be at least about 4%, preferably at least about 5% and most preferably at least about 6% relative to the sulfosuccinate surfactant.

Although the addition of sulfosuccinate or its salt in the composition can have a slight effect in increasing the initial viscosity of the compositions, the inventors have surprisingly found sulfosuccinate or its salt has a much larger than expected effect in preventing an increase in the viscosity of the composition after storage, especially storage at elevated temperatures. Thus, the sulfosuccinate acts as a storage stabilizing agent and maintains the viscosity of the composition approximately at its initial value before storage. By the term "maintains the viscosity at its initial value" is meant that the viscosity of the composition after storage is not obviously different to an untrained observer in the course of normal use of the composition. To achieve this level of viscosity "maintenance" generally requires that the viscosity after storage does not vary (i.e., increase) by more than about 75% of its initial value, and preferably is within about 65% of its initial value. Thus, the level of sulfosuccinic acid is chosen to achieve this viscosity maintenance. This level depends on the specific composition employed but has been found to be at least about 4% relative to the sulfosuccinate surfactant.

The term "initial viscosity" refers to the viscosity of the composition after it has been prepared and stored at room temperature (approximately 25-27° C.) for a sufficient amount of time to allow equilibration. Generally, the sample is allowed to equilibrate overnight (15-24 hrs) before the initial viscosity is recorded.

As is well known, it is convenient to use as one indicator of long term storage stability, accelerated storage testing where the test composition is exposed to a higher temperature. In the present context it is preferred that the composition maintain its viscosity after storage at 49° C. for a minimum of about 4 weeks of storage and most preferably for a minimum of about 11 weeks of storage.

From the above discussion, it should be clear that the sulfosuccinic acid or salt is not acting in the mixed sulfosuccinate-amphoteric compositions of the present invention as a traditional viscosity regulator since it has a marginal effect on the viscosity of the composition in the absence of storage.

There are two main routes for the introduction of the sulfosuccinic acid (or sulfosuccinic acid salt). The first is as a component of the commercial sulfosuccinate surfactant, either as residual reactant or as a hydrolysis product. The second is by separate and direct addition of the sulfosuccinic acid or its salt to the composition. Of course a combination of these two addition routes can also be employed to achieve the viscosity maintenance level described above. Regardless of how the sulfosuccinic acid is introduced, its total level expressed as a weight % of sulfosuccinic acid relative to the total weight of the sulfosuccinate surfactant should exceed the critical value set forth above.

Optional Ingredients

Buffering Agents

The pH of the composition desirably ranges from about 5 to about 7, preferably between about 6 and about 6.5 and most preferably between about 6.1 and about 6.4.

It is also preferable to achieve an adequate acid buffer capacity to resist pH changes, as this has been found to improve the physical storage stability of the composition.

The acid buffer capacity is defined as the number of moles of acid (e.g., protons or hydronium ions) that can be added to one liter of the composition to result in a drop in pH by 1 pH unit. The acid buffer capacity can be measured by titration of the test composition (generally a 10-fold dilution) with a standard solution of a strong acid such as HCl using a pH electrode. In practice, it has been found the acid buffer capacity of the composition be at least about 0.01 moles hydrodium ion, preferably at least about 0.02 moles, and most preferably at least about 0.03 moles per liter of composition.

A variety of acid/base pairs can be used as the buffer system as is well known in the art. Particularly suitable buffers are citric acid neutralized with sodium or ammonium hydroxide and polyacrylic acid neutralized with sodium or ammonium hydroxide.

Conditioning Agents

The compositions of this invention can also contain one or more conditioning agents selected from silicone conditioning agents and non-silicone conditioning agents.

Conditioning agents present in the compositions in droplet or particulate form, that can be liquid, semi-solid or solid in nature, so long as they are substantially uniformly dispersed in the fully formulated product. Any droplets of oily conditioning agent are preferably present as either liquid or semi-solid droplets, more preferably as liquid droplets.

i) Silicone Conditioning Agents

The compositions of the present invention can further include a silicone conditioning agent at concentrations effective to provide hair and skin conditioning benefits. Such concentrations range from about 0.01% to about 5%, preferably from about 0.1% to about 5%, and most preferably from about 0.1% to about 3%, by weight of the shampoo compositions.

The silicone conditioning agents are preferably water insoluble and non-volatile silicones but water soluble and volatile silicones can also be utilized. Typically the silicone will be intermixed in the composition so as to be in the form of a separate, discontinuous phase of dispersed, insoluble particles, also referred to as droplets. These droplets are typically suspended with an optional suspending agent described hereinafter. The silicone conditioning agent phase may comprise a silicone fluid conditioning agent and can also comprise other ingredients, such as a silicone resin to improve silicone fluid deposition efficiency or enhance glossiness (especially when employing high refractive index silicones).

Suitable silicones include polydiorganosiloxanes, in particular polydimethylsiloxanes that have the CTFA designation dimethicone. Also suitable for use in compositions of the invention (particularly shampoos and conditioners) are polydimethyl siloxanes having hydroxyl end groups, which have the CTFA designation dimethiconol.

Also suitable for use in compositions of the invention are silicone gums or resins having a slight degree of cross-linking, as are described for example in WO 96/31188. In the case of hair applications, these materials can impart body, volume and stylability to hair, as well as good wet and dry conditioning. Examples of such materials are those offered by General Electric as GE SS4230 and GE SS4267. Commercially available silicone resins will generally be supplied in a dissolved form in a low viscosity volatile or nonvolatile silicone fluid but they can also be used as preformed emulsions.

Another category of nonvolatile, insoluble silicone fluid conditioning agent is the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums. The high refractive index polysiloxane fluids contain a sufficient amount of aryl-containing substituents to increase the refractive index to the desired level, which is described above.

The viscosity of the emulsified silicone itself (not the emulsion or the final hair or skin conditioning composition) is typically at least 10,000 cst, preferably at least 60,000 cst, most preferably at least 500,000 cst, ideally at least 1,000,000 cst. Preferably the viscosity does not exceed 10,000,000 cst for ease of formulation.

Emulsified silicones for use in the compositions of the invention will typically have an average silicone droplet size ranging from about 0.1 µm to about 100 µm. For shampoo applications a smaller silicone droplet size is preferable, generally less than 30, preferably less than 20, more preferably less than 10 µm. Conversely, for body wash applications a larger droplet size, ranging from about 50 µm, to above 100 µm can be employed.

Suitable silicone emulsions for use in the invention are also commercially available in a pre-emulsified form either as conventional or as microemulsions. Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

It has been reported in WO9953889 that utilizing a combination of emulsified silicone and microemulsified silicone, in the shampoo composition can significantly boost the conditioning performance of silicone in a surfactant-based shampoo composition. The weight ratio of emulsified particles of silicone to microemulsified particles of silicone suitably ranges from 4:1 to 1:4. Preferably, the ratio of emulsified particles of silicone to microemulsified particles of silicone ranges from 3:1 to 1:3, more preferably from 2:1 to 1:1.

A further preferred class of silicones for inclusion especially in shampoos and conditioners of the invention are amino functional silicones. By "amino functional silicone" is meant a silicone containing at least one primary, secondary or tertiary amine group, or a quaternary ammonium group. These will typically have a mole % amine functionality in the range of from about 0.1 to about 8.0 mole %, preferably from about 0.1 to about 5.0 mole %, most preferably from about 0.1 to about 2.0 mole %.

Examples of suitable amino functional silicones include polysiloxanes having the CTFA designation "amodimethicone", amino functional silicones termed "trimethylsilylamodimethicone", aminofunctional copolymers of dimethicone and polyalkyleneoxide such as SILSOFT TONE from General Electric Specialty Materials (formally available from OSI), and the quaternary silicone polymers described in EP-A-0 530 974.

The viscosity of the amino functional silicone is not particularly critical and can suitably range from about 100 to about 500,000 cst.

Also suitable are emulsions of amino functional silicone oils with non ionic and/or cationic surfactant. Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning). Microemulsified amino silicones are also highly suitable.

For shampoo compositions intended for the treatment of "mixed" hair (i.e. greasy roots and dry ends), it is preferred to use a combination of amino functional and non-amino functional silicone in compositions of the invention. In such a case, the weight ratio of amino functional silicone to non-amino functional silicone will typically range from 1:2 to 1:20, preferably 1:3 to 1:20, more preferably 1:3 to 1:8.

Although non-volatile silicones are preferred in the present composition, volatile silicone, which imparts additional attributes such as gloss to the hair are also suitable. Preferably, the volatile silicone conditioning agent has an atmospheric pressure boiling point less than about 220° C. The volatile silicone conditioner is present in an amount of from 0% to about 3%, preferably from about 0.25% to about 2.5%, and more preferably from about 0.5% to about 1.0%, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation.

Examples of less preferred but suitable water soluble nonvolatile silicones nonexclusively include cetyl triethylammonium dimethicone copolyol phthalate, stearalkonium dimethicone copolyol phthalate, dimethicone copolyol and mixtures thereof.

Especially preferred silicones conditioning agents include: dimethiconol emulsion, 60% active from Dow Corning, DC1785 (approximately 1 μm average particle size, e.g., $D_{32}$); dimethiconol emulsion, 40% active from Dow Corning, DC 1786 (approximately 0.3 μm average particle size); dimethiconol emulsion, 50% active from Dow Corning, DC 1788 (approximately 0.3 μm average particle size); amodimethicone emulsion, 35% active from Dow Corning, DC 939 (approximately 0.3 μm average particle size); amodimethicone microemulsion from General Electric, SME 253 (approximately 20 nm average particle size); and a silicone gum-amodimethicone blend from Basildon Silicones, PCP 2056S (approximately 1 μm average particle size).

In compositions comprising silicone, it is preferred that a suspending agent for the silicone also be present. Suitable suspending agents are described separately below.

ii) Non-silicone Oily Conditioning Components

Compositions according to the present invention may also contain a dispersed, non-volatile, water-insoluble oily conditioning agent. By "water-insoluble" is meant that the material is not soluble in water (distilled or equivalent) at a concentration of 0.1% (w/w), at 250° C.

Suitably, the $D_{3,2}$ average droplet size of the oily conditioning component is at least 0.4, preferably at least 0.8, and more preferably at least 1 μm.

Oily or fatty materials or their mixtures are preferred conditioning agents in the compositions of the invention. Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as C2-C6 alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methyinonane, polybutene, such as the copolymer of isobutylene and butene. Particularly preferred hydrocarbon oils are the various grades of mineral oils, and petrolatum especially for skin care applications.

Suitable fatty esters are characterized by having at least 10 carbon atoms, and include esters with hydrocarbyl chains derived from fatty acids or alcohols, e.g., monocarboxylic acid esters, polyhydric alcohol esters, and di- and tricarboxylic acid esters.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Di- and trialkyl and alkenyl esters of carboxylic acids can also be used. These include, for example, esters of C4-C8 dicarboxylic acids such as C1-C22 esters (preferably C1-C6) of succinic acid, glutaric acid, adipic acid, hexanoic acid, heptanoic acid, and octanoic acid.

Polyhydric alcohol esters such as alkylene glycol and polyalkylene glycol mono, di, and tri esters are also suitable for use in the instant compositions. Particularly preferred fatty esters are mono-, di- and triglycerides, more specifically the mono-, di-, and triesters of glycerol and long chain carboxylic acids such as C1-C22 carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.05% to 10%, preferably from about 0.2% to about 5% and more preferably from about 0.5% to about 3%.

Cationic Polymer

Cationic polymers are optionally employed to provide enhanced deposition of the non-volatile, water-insoluble silicone as well as conditioning benefits in their own right. The level of cationic polymer in the composition can be in the range from about 0.01 to about 2%, preferably from about 0.1 to about 0.6%, and most preferably from about 0.15 to about 0.45%.

The cationic conditioning polymer contains cationic nitrogen-containing groups such as quaternary ammonium or protonated amino groups. The cationic protonated amines can be primary, secondary, or tertiary amines (preferably secondary or tertiary), depending upon the particular species and the selected pH of the shampoo composition. The average molecular weight of the cationic conditioning polymers is between about 10 million and about 5,000. The polymers also have a cationic charge density ranging from about 0.2 meq/gm to about 7 meq/gm.

Any anionic counterions can be use in association with the cationic conditioning polymers so long as the polymers remain soluble or readily dispersible in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the composition includes homopolymers, copolymers, terpolymers, and so forth, of quaternary ammonium or cationic amine-substituted monomer units, optionally in combination with non-cationic monomers referred to herein as spacer monomers. Non-limiting examples of such polymers are described in the CTFA Cosmetic Ingredient Dictionary, 6th edition, edited by Wenninger, J A and McEwen Jr, G N, (The Cosmetic, Toiletry, and Fragrance Association, 1995), which description is incorporated herein by reference. Particularly suitable cationic polymers for use in the composition include polysaccharide polymers, such as cationic cellulose derivatives, cationic starch derivatives, and cationic guars.

Examples of cationic cellulose polymers are those available from Amerchol Corp. (Edison, N.J.,) in their POLY-MER JR and LR series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose treated with lauryl dimethyl ammonium-substituted epoxide, referred to in the industry (CTFA) as Polyquaternium 24. These materials are available from Amerchol Corp. (Edison, N.J.,) under the trade name Polymer LM-200.

An especially preferred cationic polymer is cationic guar gum derivatives, such as guar hydroxypropyltrimonium chloride, specific examples of which include the JAGUAR series commercially available from Rhodia Corporation (e.g., JAGUAR EXCEL or JAGUAR C13S). Other suitable cationic polymers include quaternary nitrogen-containing cellulose ethers, some examples of which are described in U.S. Pat. No. 3,962,418, which description is incorporated herein by reference. Other suitable cationic polymers include copolymers of etherified cellulose, guar and starch, some examples of which are described in U.S. Pat. No. 3,958,581, which description is incorporated herein by reference.

Non limiting examples of suitable optional synthetic cationic polymers include copolymers of vinyl monomers having cationic protonated amine or quaternary ammonium functionality with water soluble spacer monomers such as acrylamide, methacrylamide, alkyl and dialkyl acrylamides, alkyl and dialkyl methacrylamides, alkyl acrylate, allyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Other suitable optional synthetic polymers include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloyalyl ammonium salt, dialyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Still other suitable optional synthetic polymers for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A) under the LUVI-QUAT tradename (e.g., LUVIQUAT FC 370); copolymers of 1-vinyl-2-pyrrolidone and dimethylaminoethyl methacrylate (refereed to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms.

Thickening and Suspending Agents

The compositions of the present invention preferably further incorporate thickening/suspending agents to ensure that insoluble materials are stable. A variety of materials can be employed. These include swelling and associative polymers, finely divided crystalline or amorphous inorganic and organic materials that form networks, electrolytes and combinations thereof.

Organic polymers include carboxyvinyl polymers such as the copolymers of acrylic acid crosslinked with polyallylsucrose as described in U.S. Pat. No. 2,798, 053, which description is incorporated herein by reference. Examples of these polymers include CARBOPOL 934, 940, 941, and 956, available from NOVEON and the alkali swellable acrylic latex polymers sold by Rohm and Haas under the ACRYSOL or ACULYN trade names.

Other suitable suspending agents include xanthan gum at concentrations ranging from about 0.3% to about 3%, preferably from about 0.4% to about 1.2%, by weight of the compositions.

Other suitable polymeric suspending agents may be used in the compositions, including those that can impart a gel-like viscosity to the composition, such as water soluble or colloidally water soluble polymers like cellulose ethers (e.g., methylcellulose, hyd roxybutyl methylcellulose, hyd ropylcellulose, hyd roxypropyl methylcellu lose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Optional crystalline organic suspending agents include acyl derivatives, long chain amine oxides, or combinations thereof, concentrations of which range from about 0.1% to about 5%, preferably from about 0.5% to about 3%, by weight of the shampoo compositions. When used in the shampoo compositions, these suspending agents are present in crystalline form. These suspending agents are described in U.S. Pat. No. 4,741,855, which description is incorporated herein by reference. These suspending agents include ethylene glycol esters of fatty acids preferably having from about 16 to about 22 carbon atoms. Examples include ethylene glycol stearates, both mono and distearate, but particularly distearates containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$-$C_{22}$ chains may be used.

Examples of suitable long chain amine oxides for use as suspending agents include alkyl ($C_{16}$-$C_{22}$) dimethyl amine oxides, e.g., stearyl dimethyl amine oxide.

Another useful crystalline suspending agent is trihydroxystearin sold under the trade name THIXCIN R.

Network forming inorganic materials include but are not limited to, clays, and silicas. Examples of clays include smectite clay selected from the group consisting of bentonite and hectorite and mixtures thereof. Synthetic hectorite (laponite) clay are often used with an electrolyte salt capable of causing the clay to thicken (alkali and alkaline earth salts such as halides, ammonium salts and sulfates). Bentonite is a colloidal aluminum clay sulfate. Examples of silica include amorphous silica and include fumed silica and precipitated silica and mixtures thereof.

Associative polymers are those which incorporate hydrophobic groups which can form labile crosslinks alone or with the participation of surfactant micelles. An example of associative polymers the hydrophobically modified cross linked polyacrylates sold by NOVEON under the PEMULEN trade name. Other examples are hydrophobically modified cellulose ether and hydrophobically modified polyurethane.

A particularly preferred class of thickening and suspending agent in the present invention is hydrophobically modified water-soluble nonionic polyol. Suitable hydrophobically modified water-soluble nonionic polyols for use herein are PEG 120 methyl glucoside dioleate (available from Amercol under the trade name GLUCAMATE DOE 120), PEG-150 pentaerythrityl tetrastearate (available from Croda under the trade name CROTHIX, PEG-75 dioleate (available from Kessco under the trade name PEG-4000 DIOLEATE) and PEG-150 distearate (available from Witco under the trade name WITCONAL L32).

Long chain fatty esters of polyethylene glycol, e.g., PEG-150 distearate, are especially preferred thickening and suspending agents in the present invention. Although the PEG fatty esters can be used alone, it has been found that their effectiveness and efficiency can be greatly improved when they are combined with certain electrolytes. Especially preferred electrolytes for use in combination PEG-150 distearate, are sodium citrate and sodium chloride as they provide a synergistic thickening system that allows adequate thickening at low levels of inclusion in composition that have a low total concentration of surfactant, e.g., less than about 15 wt. %.

The above thickening and structuring agents can be used alone or in mixtures and may be present in an amount from about 0.1 wt. % to about 10 wt. % of the composition.

Storage Stabilizer Agents

In addition to sulfosuccinic acid, it has been found that electrolytes that provide certain soluble cations can also improve stability of the sulfosuccinate surfactant/amphoteric surfactant mixtures during high temperature storage. Addition of these electrolytes also helps prevent an unacceptable increase in the viscosity of compositions during storage, which appears to be an unusual property of sulfosuccinate and amphoteric surfactant mixtures. Such electrolytes are useful optional ingredients in the present invention.

Preferred electrolytes to be employed in the present invention are those which are fully dissociated in the liquid and whose constituent ions are completely dissolved. Thus, preferred electrolytes do not precipitate as different species with other components of the composition.

Preferred electrolytes are those that are highly soluble in the compositions of the invention and are the most efficient in the delivery of the required cations, and do not themselves have an adverse effect on the mildness, pH or solubility of other formulation ingredients.

Especially preferred are water-soluble salts monovalent inorganic ions, especially ammonium, sodium, and to a lesser extent potassium salts. These include the chlorides, sulfates, carbonates and various salts of weak organic acids such as citrates, glycolates, succinates and acrylate/polyacrylate salts and mixtures thereof.

The anions of the electrolyte should preferably themselves not be a surfactant molecule capable of micellization in water at the levels employed in the composition as this greatly reduces their availability in solution. Thus, if the anion is an organic molecule, it should preferably not have an unsubstituted hydrocarbon chain greater than about 5 carbon atoms.

Ammonium and sodium chloride, citrate and polyacrylate and their mixtures are the most preferred.

The exact level of electrolyte required to maintain the viscosity of the composition at its initial value (in the sense discussed above) depends upon the constituents of the composition and their levels. In particular, the level of cation depends upon the total weight percent of the sulfosuccinate surfactant used in the composition. The level of electrolyte should be greater than or equal to about 1% by weight of composition, preferably at least about 1.5% and most preferably at least about 2%.

Aesthetic and Adjunct Ingredients

A wide variety of optional ingredients can be incorporated in the formulation provided they do not interfere with the mildness and hair conditioning benefits provided by the composition. These include but are not limited to: perfumes; pearlizing and opacifying agents such as higher fatty acids and alcohols, ethoxylated fatty acids, solid esters, nacreous "interference pigments" such as $TiO_2$ coated micas; dyes and pigment coloring agents; sensates such as menthol; preservatives including anti-oxidants and chelating agents; emulsion stabilizers; auxiliary thickeners; and mixtures thereof.

Additional Hair and Skin Benefit Agents

A variety of optional ingredients can be incorporated into the compositions of the instant invention to promote hair and scalp health. However, these ingredients should be chosen to be consistent with the mildness of the composition. Potential benefit agents include but are not limited to: lipids such as cholesterol, ceramides, and pseudoceramides; additional non-silicone hair conditioning agents such as synthetic or natural hydrocarbon esters and waxes; humectants such as glycerol and sorbitol; antimicrobial agents such as zinc pyridinethione and TRICLOSAN; sunscreens such as cinnamates and mixtures thereof.

Evaluation Methodology

Formulation Viscosity Protocol

Shampoo samples contained in 6 oz glass jars were placed in a water bath set at 26.7° C. After 1 day of storage at 26.7° C., the shampoo samples were removed and their viscosity was immediately measured using a Brookfield viscometer fitted with an RV4 spindle at a rotational speed of 20 rpm. The spindle was allowed to rotate at 20 rpm for 1 minute before the viscosity measurements were recorded.

Storage Stability Testing Protocol

Shampoo samples were placed in 6 oz jars and labeled with the amount of time each was to be kept in storage. The jars of shampoo were placed in an oven set to the required storage temperature, e.g., 49° C. Once the storage time for each jar had been reached, the jars were taken out of storage and the viscosity of the stored shampoo samples were measured using the Formulation Viscosity Protocol described above.

Zein Solubility In-Vitro Assay

Zein solubility provides a simple directional indication of mildness and is widely used in the art for testing the mildness of both surfactant raw materials, shampoos and skin cleansing compositions. Zein is a protein (blends of amino acid derived from maize) which swells and denatures in response to surfactants in a similar way to skin keratin proteins. This procedure was developed on the basis that the more Zein solubilized by a given surfactant composition under standardized test conditions, the greater is the irritancy of the composition. Zein solubility is not intended as a replacement for clinical studies or the more biologically based Fluorescein Leakage In-Vitro Assay even though a reasonable correlation has been demonstrated. Therefore the principle application for Zein solubility is for initial screening where it provides a good predictor of eventual irritation potential. Under the test conditions employed and described below a Zein solubility of less than 1% is a good indicator of potentially mild compositions while a Zein solubility greater than 1% is a good indication that the composition will be irritating to the eyes.

Apparatus

Analytical balance, 100 ml beakers, stir bars, medium stir plate, 10 ml syringe, 20 ml scintillation vials, conventional oven, set at 75° C.

Procedure

1. Weigh 6.25 g of shampoo into a 100-ml beaker and dilute it to 50 g with DI water.
2. Mix the solution on a stir plate @ 300 rpm (set dial at 4 on stirring plate) until the solution looks uniform or the entire sample is dissolved.
3. Record the pH of the solution.
4. Withdraw 6 ml of solution using a syringe.
5. Filter solution through a 0.45-micron syringe filter onto a scintillation vial.
6. Cap the vial and label it as blank. A blank is needed to correct for any soluble material.
7. Add 2 g of Zein to the remaining solution and equilibrate for 1 hour at constant stirring speed (300 rpm). After 10 minutes of stirring, if all or most of the Zein dissolved, add an additional 1 g of Zein. Keep adding more Zein in 1 g increments every 5-10 minutes until there is undissolved Zein floating in the solution.
8. After 1 hour of constant stirring, allow solution to settle for 5 minutes.
9. Withdraw 6 ml of the supernatant solution using a syringe and filter it through a 0.45 micron syringe filter onto a scintillation vial.
10. Cap the vial and label it as sample.
11. Perform nonvolatile on both samples using a conventional oven set at 75° C. Allow samples to dry overnight.
12. Calculate the percent Zein dissolved.

Calculation

% Zein solubilized=% nonvolatile of sample−% nonvolatile of blank

Subjective Lather Assessment Panel

The overall lather of test shampoo compositions was assessed subjectively by a naive panel composed of at least 10 participants employing tresses of hair. The test protocol was as follows:

1) Adjust water temperature to 40° C.
2) First wet hands and hair tresses (4 gm tresses of hair)
3) Apply 0.5 ml of shampoo (premeasured in syringe)
4) Massage hair tresses for 1 minute to evaluate lather.
5) Rinse tresses thoroughly, and then repeat above steps for next shampoo sample.
6) After treating the tresses with all four shampoos, rank the lather of each shampoos from best lather (4) to worst lather (1).

Note: Order of samples given to participants was randomized for each participant.

EXAMPLES

The following examples are shown as illustrations of the invention and are not intended in any way to limit its scope.

Example 1

This example illustrates the criticality of the ratio of sulfosuccinic acid to sulfosuccinate surfactant on storage stability.

Examples Ex 1A through Ex 1H, whose compositions are given in Table 1 were prepared as follows by the combination of the premixes described below:

A. Premix Preparation

Carbomer 980 Premix (A) as required: This premix is formed by dissolving Carbomer 980 in water at room temperature and mixing until completely hydrated and dissolved (no lumps of "fisheyes").

Jaguar C13S Premix (B) (or other cationic polymer) is prepared by mixing Jaguar C13S in propylene glycol for 10 minutes or until completely dissolved and uniform.

Ammonium Chloride(or NaCl)/Sodium Citrate Dihydrate 25 wt. % Premix (C) is prepared by adding ammonium chloride (or sodium chloride) and sodium citrate dihydrate to water and mixing until completely dissolved.

PEG-150 Distearate (5 wt. %) Premix (D) is prepared by addition to a portion of the CAPB (or other amphoteric surfactant) solution heated to 65° C. The mixture is cooled to room temperature and additional water added as required.

B. Main Batch Preparation:

Water is added to the mixer followed by the addition of the Carbomer Premix (A). Under mixing optional surfactants such as Sodium Laureth Sulfate are added as required (e.g., SLES-1, 70%) and mixed until dispersed. The Jaguar C13s Premix (B) is then added and the batch is mixed at 100 rpm 30 minutes. Disodium Laureth Sulfosuccinate is then added and dispersed followed by the addition of the remaining amphoteric. Pearlizer, silicone, preservatives and sodium hydroxide are then added and dispersed. This is followed by the Ammonium Chloride(or NaCl)/Sodium Citrate Dihydrate Premix (C). The viscosity and pH are then measured and adjusted with additional salt, ppg-9, or PEG-150DS Premix (D) and NaOH or Citric Acid respectively.

It is seen that the level of sulfosuccinic acid has a much greater effect in preventing the viscosity of compositions stored at an elevated temperature from increasing than it has on the initial viscosity of the composition. In fact, the viscosity of the compositions stored at room temperature for the same period of time hardly changes from its initial value (not shown). Thus, sulfosuccinic acid is not acting as a typical viscosity regulator in the conventional sense but rather as a highly specific storage stabilizing agent, especially storage at elevated temperature.

Storage at an elevated temperature is widely used as an accelerated test of storage stability at ambient conditions, i.e., shelf-life. An increase in viscosity of less than about 75% of the initial value is still acceptable in compositions having an initial viscosity of about 5000-7000 CPS, i.e., the compositions of Table 1. It is noted from Table 1 that a level of at least about 4% sulfosuccinic acid relative to the sulfoccinate surfactant is required in the composition to maintain the viscosity after storage below this threshold.

Example 2

This examples demonstrates that the combination of the sulfosuccinate and amphoteric surfactants produces the increase in viscosity.

TABLE 1

Compositions and Physical Properties of Example 1

| Ingredients | Ex 1A | Ex 1B | Ex 1C | Ex 1D | Ex 1E | Ex 1F | Ex 1F |
|---|---|---|---|---|---|---|---|
| Lauryl ethoxy sulfate (1EO) | 6 | 6 | 6 | 6 | 6 | 6 | 6 |
| Disodium laureth sulfosuccinate | 4 | 4 | 4 | 4 | 4 | 4 | 4 |
| Cocoamidopropyl betaine | 3 | 3 | 3 | 3 | 3 | 3 | 3 |
| Sulfosuccinic acid | 0.163 | 0.238 | 0.46 | 0.56 | 0.6 | 0.625 | 0.687 |
| Carbopol (Carbomer 980) | 0.4 | 0.4 | 0.4 | 0.4 | 0.4 | 0.4 | 0.4 |
| Silicone Emulsion (Silicone Gum/ Amodimethicone blend PCP2056S) | 1.5 | 1.5 | 1.5 | 1.5 | 1.5 | 1.5 | 1.5 |
| Cationic Guar (Jaguar C13S) | 0.2 | 0.2 | 0.2 | 0.2 | 0.2 | 0.2 | 0.2 |
| Pearlizer (Mirasheen CP920; Rhodia) | 6.5 | 6.5 | 6.5 | 6.5 | 6.5 | 6.5 | 6.5 |
| Ammonium chloride | 2.0 | 2.0 | 2.0 | 2.0 | 2.0 | 2.0 | 2.0 |
| Sodium Citrate | 0.5 | 0.5 | 0.5 | 0.5 | 0.5 | 0.5 | 0.5 |
| Minors fragrance, preservatives, dyes | 0.22 | 0.22 | 0.22 | 0.22 | 0.22 | 0.22 | 0.22 |
| Water | to 100 | to 100 | to 100 | to 100 | to 100 | to 100 | to 100 |
| pH (adjusted with NaOH) | 6.3 | 6.3 | 6.3 | 6.3 | 6.3 | 6.3 | 6.3 |
| Sulfosuccinic acid level as a % of sulfosuccinate surfactant | 4.1 | 5.9 | 11.5 | 14.0 | 15.0 | 15.6 | 17.2 |
| Initial Viscosity (cps) | 6200 | 5700 | 5500 | 4300 | 5200 | 4000 | 5000 |
| Final Viscosity after 11 weeks at 49° C. | 10800 | 9500 | 8200 | 6500 | 6700 | 6000 | 7000 |
| Viscosity Increase after 11 weeks storage @ 49° C. | 4600 | 3800 | 2700 | 2200 | 1500 | 2000 | 2000 |
| % Increase in viscosity after storage from initial value | 74% | 67% | 49% | 51% | 29% | 50% | 40% |

The initial viscosity of the example compositions and the change in viscosity after storage are also recorded at the bottom of Table 1 together with the % sulfosuccinic acid relative to the sulfosuccinate surfactant.

Example Ex 2A and EX 2B and comparative examples C2A-C2D whose compositions are given in Table 2, were prepared according to the methods described in Example 1.

TABLE 2

Compositions and Physical Properties for Example 2

| Ingredients | Ex2A | Ex2B | C2A | C2B | C2C |
|---|---|---|---|---|---|
| | Wt. % | | | | |
| Lauryl ethoxy sulfate (1EO) | 6 | 6 | 6 | 6 | 6 |
| Disodium laureth sulfosuccinate | 4 | 4 | 4 | 4 | |
| Cocoamidopropyl betaine | 3 | 3 | | | 3 |
| Sulfosuccinic acid | 0.163 | 0.46 | 0.163 | 0.46 | 0 |
| Silicone/Aminosilicone blend | 1.5 | 1.5 | 1.5 | 1.5 | 1.5 |
| Cationic Guar (Jaguar C13S) | 0.2 | 0.2 | 0.2 | 0.2 | 0.2 |
| Pearlizer (Mirasheen CP920; Rhodia) | 6.5 | 6.5 | 6.5 | 6.5 | 6.5 |
| Carbopol (Carbomer 980) | 0.4 | 0.4 | 0.4 | 0.4 | 0.4 |
| Ammonium chloride | 2.0 | 2.0 | 2.0 | 2.0 | 2.0 |
| Minors, fragrance, preservatives, dyes | 0.22 | 0.22 | 0.22 | 0.22 | 0.22 |
| Water | to 100 | to 100 | to 100 | to 100 | to 100 |
| pH (adjusted with NaOH) | 6.3 | 6.3 | 6.3 | 6.3 | 6.3 |
| Sulfosuccinic acid level as a % of sulfosuccinate | 4.1 | 11.5 | 4.1 | 14.1 | 0 |
| Viscosity Increase after 11 weeks storage @ 49° C. | 4,600 | 2,700 | 1,488[a] | 704[a] | −406[a] |

[a]Extrapolated values based on 4 week storage data @ 49° C.

The change in viscosity after accelerated storage (11 weeks @ 49° C.) are recorded at the bottom of Table 2 together with the % sulfosuccinic acid relative to the sulfosuccinate surfactant. Several points are noteworthy.

Most surprisingly, the largest increases in viscosity after accelerated storage only occurs in compositions that contain both the sulfosuccinate surfactant and the amphoteric surfactant—in this case a betaine (compare Ex 2A and Ex 2B with C2A-C2C). Furthermore, it is in such combinations where the level of sulfosuccinic acid is critical (compare viscosity after storage of Ex 2A with Ex 2B).

In contrast, compositions that do not contain the amphoteric and the sulfosuccinate surfactant do not exhibit such large increases in viscosity after storage and their viscosity does not respond to sulfosuccinate level (compare viscosity after storage of comparative examples C2A-C2C). Thus, sulfosuccinic acid is not acting as a typical "generic" viscosity regulator and its action is highly specific to the sulfosuccinate surfactant/amphoteric surfactant compositions disclosed herein.

Example 3

This example illustrates the effect on mildness and lather of combining a sulfosuccinate surfactant with an amphoteric surfactant.

Example Ex 3 and comparative examples C3A-C3C whose compositions are given in Table 3, were prepared by the methods described in Example 1.

TABLE 3

Compositions and Physical Properties for Example 3

| Ingredients | Ex 3 | C3A | C3B | C3C |
|---|---|---|---|---|
| | Wt. % | | | |
| Lauryl ethoxy sulfate (1EO) | 6 | | 13 | 6 |
| Disodium laureth sulfosuccinate | 4 | 13 | | 7 |
| Cocoamidopropyl betaine | 3 | | | |
| Sulfosuccinic acid | 0.56 | 1.8 | 0.56 | 0.98 |
| Silicone Emulsion (Silicone Gum/Amodimethicone blend PCP2056S) | 1.5 | 1.5 | 1.5 | 1.5 |
| Cationic Guar (Jaguar C13S) | 0.2 | 0.2 | 0.2 | 0.2 |
| Pearlizer (Mirasheen CP920; Rhodia) | 6.5 | 6.5 | 6.5 | 6.5 |
| Ammonium chloride | 2 | 2 | 2 | 2 |
| Minors fragrance, preservatives, dyes | 0.22 | 0.22 | 0.22 | 0.22 |
| Water | to 100 | to 100 | to 100 | to 100 |
| pH (adjusted with NaOH) | 6.3 | 6.3 | 6.3 | 6.3 |
| Sulfosuccinic acid level as a % of sulfosuccinate | 14.0 | 14.0 | 0 | 14.0 |
| Average Lather Score | 3.2 | 1.4 | 3.4 | 2.0 |
| In-Vitro Mildness (zein solubility) | 1.8 | 2.1 | 3.07 | 2.41 |

The Average Lather Score (as measured by the Subjective Lather Assessment Panel described above in the METHODOLOGY SECTION), and the in-vitro mildness (as measured by the Zein Solubility Test also described above in the METHODOLOGY SECTION) are recorded at the bottom of Table 3.

It is clear from the results that of all the surfactant combinations tested, the combination of an alkyl ethoxy sulfate, a sulfosuccinate surfactant and an amphoteric surfactant (Ex 3) has the lowest Zein solubility and thus should be mildest. Furthermore, this combination has excellent lather and thus does not sacrifice in-use properties and efficiency for mildness (compare Ex 3 with C3B).

This example thus demonstrates the desirability of combinations of sulfosuccinate surfactant and amphoteric surfactant for cleansing human hair and skin and the relevance of solving the storage stability problems intrinsic in such combinations.

Based on mildness (Zein solubility) and lather performance, a particularly preferred embodiment of the invention is a composition consisting essentially of:

| | |
|---|---|
| Disodium laureth sulfosuccinate | 2%-6% |
| Cocoamidopropyl betaine | 2%-5% |
| Lauryl ethoxy sulfate (1-3 EO) | 5%-9% |
| Sulfosuccinic acid | 4%-20% (based on the sulfosuccinate surfactant) | that provides a Zein solubility of less than or equal to 2 measured by the Zein Solubility Test, and Average Lather Score of at least 3 measured by the Subjective Lather Assessment Panel.

The term "consisting essentially of" as used in the present context, means that various optional ingredients can be included so long as they do not compromise (i.e., reduce) the mildness and lather performance of the composition below the threshold values defined above. Useful optional ingredients include:

| | |
|---|---|
| Ammonium chloride and/or sodium chloride | 0%-2.5% |
| Sodium citrate | 0%-2% |
| Cationic polymer | 0%-1% |
| Silicone | 0%-5% |
| Thickener | 0%-10% |
| Aesthetic adjuvants (color, perfume, biocides etc.) | 0%-5% |

Examples 4-6 are meant to illustrate some of the varied compositions useful in the instant invention but are in no way meant to limit the scope of sensory additives, adjuncts and benefit agents that can be employed.

Example 4

The compositions in Table 4 illustrate different surfactant systems of the invention.

TABLE 4

Example of Different Surfactant Systems of Invention

| | Wt. % | | | | | | | |
|---|---|---|---|---|---|---|---|---|
| Ingredients | Ex 4A | Ex 4B | Ex 4C | Ex 4D | Ex 4E | Ex 4F | Ex 4G | Ex 4H |
| Sodium Laureth Sulfate (1EO) | 6.0 | 10.0 | | | 5.0 | 7.0 | 5.0 | 6.0 |
| Sodium Laureth Sulfate (2EO) | | | | 8.0 | | | | |
| Disodium Laureth Sulfosuccinate | 4.0 | 6.7 | 10.0 | 2.0 | 4.0 | 4.0 | 5.0 | 4.0 |
| Cocamidopropyl Betaine | 3.0 | 5.0 | 7.5 | 3.0 | | | 2.0 | 2.0 |
| Hydroxysultaine | | | | | 3.0 | | 2.0 | |
| Lauroamphoacetate | | | | | | 3.0 | | 1.0 |
| Carbopol 980 | 0.40 | 0.40 | 0.40 | 0.40 | 0.40 | 0.40 | 0.40 | 0.40 |
| Jaguar C13S | 0.10 | 0.10 | 0.10 | 0.10 | 0.10 | 0.10 | 0.10 | 0.10 |
| Polyox WSR308 | 0.025 | 0.025 | 0.025 | 0.025 | 0.025 | 0.025 | 0.025 | 0.025 |
| Methocel 40-0202 | 0.3 | 0.3 | 0.3 | 0.3 | 0.3 | 0.3 | 0.3 | 0.3 |
| Glycerine | 1.000 | 1.000 | 1.000 | 1.000 | 1.000 | 1.000 | 1.000 | 1.000 |
| L-Lysine Hydrochloride | 0.010 | 0.010 | 0.010 | 0.010 | 0.010 | 0.010 | 0.010 | 0.010 |
| Silk Amino acids | 0.010 | 0.010 | 0.010 | 0.010 | 0.010 | 0.010 | 0.010 | 0.010 |
| Borage Extract | 0.001 | 0.001 | 0.001 | 0.001 | 0.001 | 0.001 | 0.001 | 0.001 |
| Mirasheen CP920; Rhodia | 6.50 | 6.50 | 6.50 | 6.50 | 6.50 | 6.50 | 6.50 | 6.50 |
| DC1788 | 0.65 | 0.65 | 0.65 | 0.65 | 0.65 | 0.65 | 0.65 | 0.65 |
| SME253 | 0.10 | 0.10 | 0.10 | 0.10 | 0.10 | 0.10 | 0.10 | 0.10 |
| Perfume | 0.80 | 0.80 | 0.80 | 0.80 | 0.80 | 0.80 | 0.80 | 0.80 |
| DMDM Hydantoin | 0.10 | 0.10 | 0.10 | 0.10 | 0.10 | 0.10 | 0.10 | 0.10 |
| Kathon CG | 0.04 | 0.04 | 0.04 | 0.04 | 0.04 | 0.04 | 0.04 | 0.04 |
| Versene 100 | 0.20 | 0.20 | 0.20 | 0.20 | 0.20 | 0.20 | 0.20 | 0.20 |
| NaOH, 50% | 0.40 | 0.40 | 0.40 | 0.40 | 0.40 | 0.40 | 0.40 | 0.40 |
| Sulfosuccinic acid | 0.18 | 0.335 | 0.65 | 0.08 | 0.2 | 0.4 | 0.3 | 0.18 |
| $NH_4Cl$ | 2.00 | 2.00 | 2.00 | 2.00 | 2.00 | 2.00 | 2.00 | 2.00 |
| PPG-9 | 0.35 | 0.35 | 0.35 | 0.35 | 0.35 | 0.35 | 0.35 | 0.35 |
| Soft Water | To 100% | To 100% | To 100% | To 100% | To 100% | To 100% | To 100% | To 100% |

Example 5

The compositions in Table 5 illustrate different conditioning systems of the invention.

TABLE 5

Example of Different Conditioning Systems of Invention

| Ingredients | Ex 5A | Ex 5B | Ex 5C | Ex 5D | Ex 5E | Ex 5F | Ex 5G |
|---|---|---|---|---|---|---|---|
| Carbopol 980 | 0.40 | 0.40 | 0.4 | 0.40 | 0.40 | 0.40 | 0.40 |
| Sodium Laureth Sulfate (1EO) | 6.0 | 6.0 | 6.0 | 6.0 | 6.0 | 6.0 | 6.0 |
| Disodium Laureth Sulfosuccinate | 4.0 | 4.0 | 4.0 | 4.0 | 4.0 | 4.0 | 4.0 |
| Cocamidopropyl Betaine | 3.0 | 3.0 | 3.0 | 3.0 | 3.0 | 3.0 | 3.0 |
| Jaguar C13S | 0.10 | 0.20 | 0.20 | 0.20 | 0.20 | 0.20 | 0.20 |
| Polyox WSR308 | | | | | 0.025 | | 0.025 |
| Methocel 40-0202 | | | | | | 0.3 | 0.3 |
| Polyox WSR-N-60K | | | | 0.025 | | | |
| Mirasheen CP920; Rhodia | 6.50 | 6.50 | 6.50 | 6.50 | 6.50 | 6.50 | 6.50 |
| DC1788 | 0.65 | | 1.30 | | | | |
| SME253 | 0.10 | 0.20 | 0.20 | 0.20 | 0.20 | 0.20 | 0.20 |
| DC7036 | — | 1.30 | — | 1.30 | 1.30 | 1.30 | 1.30 |
| Glycerine | 1.000 | 1.000 | 1.000 | 1.000 | 1.000 | 1.000 | 1.000 |
| Perfume | 0.80 | 0.80 | 0.80 | 0.80 | 0.80 | 0.80 | 0.80 |
| DMDM Hydantoin | 0.10 | 0.10 | 0.10 | 0.10 | 0.10 | 0.10 | 0.10 |
| Kathon CG | 0.04 | 0.04 | 0.04 | 0.04 | 0.04 | 0.04 | 0.04 |
| Versene 100 | 0.20 | 0.20 | 0.20 | 0.20 | 0.20 | 0.20 | 0.20 |
| NaOH, 50% | 0.40 | 0.40 | 0.40 | 0.40 | 0.40 | 0.40 | 0.40 |
| Sulfosuccinic acid | 0.16 | 0.2 | 0.28 | 0.18 | 0.24 | 0.16 | 0.4 |
| NH4Cl | 2.00 | 1.5 | 2.00 | 1.5 | 1.4 | 2.00 | 1.00 |
| NaCl | | 0.6 | | 0.8 | 0.3 | | 1.0 |
| Sodium citrate | | 0.25 | | | 1.0 | | 0.6 |
| PPG-9 | 0.60 | 0.35 | 0.20 | 0.35 | 0.35 | 0.35 | 0.35 |
| Soft Water | To 100% | To 100% | To 100% | To 100% | To 100% | To 100% | To 100% |

Example 6

The compositions in Table 6 illustrate different benefit agents of the invention.

TABLE 6

Example of Different Benefit Agents of Invention

| Ingredients | Ex 6A | Ex 6B | Ex 6C |
|---|---|---|---|
| Carbopol 980 | 0.40 | 0.40 | 0.40 |
| Sodium Laureth Sulfate (1EO) | 6.0 | 6.0 | 6.0 |
| Disodium Laureth Sulfosuccinate | 4.0 | 4.0 | 4.0 |
| Cocamidopropyl Betaine | 3.0 | 3.0 | 3.0 |
| Jaguar C13S | 0.20 | 0.20 | 0.20 |
| Polyox WSR308 | 0.025 | 0.025 | 0.025 |
| Methocel 40-0202 | 0.3 | 0.3 | 0.3 |
| Glycerine | 1.000 | 1.000 | 1.000 |
| L-Lysine Hydrochloride | | 0.010 | 0.010 |
| Silk Amino acids | 0.010 | | 0.010 |
| Borage Extract | | | 0.001 |
| Mirasheen CP920; Rhodia | 6.50 | 6.50 | 6.50 |
| SME253 | 0.20 | 0.20 | 0.20 |
| DC7036 | 1.30 | 1.30 | 1.30 |
| Perfume | 0.80 | 0.80 | 0.80 |
| DMDM Hydantoin | 0.10 | 0.10 | 0.10 |
| Kathon CG | 0.04 | 0.04 | 0.04 |
| Versene 100 | 0.20 | 0.20 | 0.20 |
| NaOH, 50% | 0.40 | 0.40 | 0.40 |
| NH4Cl | 2.1 | 1.6 | 2.00 |
| Sodium citrate | | 0.75 | 0.2 |
| PPG-9 | 0.35 | 0.35 | 0.35 |
| Soft Water | To 100% | To 100% | To 100% |

What is claimed is:

1. A mild aqueous composition suitable for cleansing hair and skin consisting of:
   v) about 2% to about 6% disodium laureth sulfosuccinate,
   vi) about 2% to about 7.5% cocoamidopropyl betaine,
   vii) about 5% to about 9% lauryl ethoxy sulfate,
   viii) about 0.8% to about 1.2% sulfosuccinic acid salt,
   ix) 0% to about 2.5% ammonium chloride or sodium chloride,
   x) 0% to about 2% sodium citrate,
   xi) 0% to about 1% of a cationic polymer,
   xii) 0% to about 5% of a silicone,
   xiii) 0% to about 1% of a thickener, and
   xiv) 0% to about 5% of an aesthetic adjuvant,
   wherein the ratio of the disodium laureth sulfosuccinate to cocamidopropyl betaine is in the range from about 1.5:1 to about 1:1.25, and wherein the weight ratio lauryl ethoxy sulfate to disodium laureth sulfosuccinate is in the range from about 2:1 to about 1:1.

* * * * *